United States Patent
Dilger

(12) 
(10) Patent No.: US 6,222,366 B1
(45) Date of Patent: Apr. 24, 2001

(54) HIGH FREQUENCY MEASURING CIRCUIT WITH INHERENT NOISE REDUCTION FOR RESONATING CHEMICAL SENSORS

(75) Inventor: John P. Dilger, Marshalltown, IA (US)

(73) Assignee: Fisher Controls International, Inc., Austin, TX (US)

( * ) Notice: Subject to any disclaimer, the term of this patent is extended or adjusted under 35 U.S.C. 154(b) by 0 days.

(21) Appl. No.: 09/310,008

(22) Filed: May 10, 1999

(51) Int. Cl.[7] .................................................. G01V 3/00
(52) U.S. Cl. ..................... 324/319; 324/322; 324/300; 73/24.06
(58) Field of Search ................... 324/319, 322, 324/300; 73/24.06, 54.41, 599

(56) References Cited

U.S. PATENT DOCUMENTS

| | | | |
|---|---|---|---|
| 3,260,104 | 7/1966 | King, Jr. | 73/23 |
| 3,863,495 | 2/1975 | Schultz et al. | 73/61.1 |
| 5,065,140 | 11/1991 | Neuburger | 340/634 |
| 5,501,986 | 3/1996 | Ward et al. | 436/525 |
| 5,604,335 | 2/1997 | Isahaya | 177/210 |
| 5,705,399 | 1/1998 | Larue | 436/501 |
| 5,817,921 | 10/1998 | Tom et al. | 73/24.01 |
| 5,918,258 | * 6/1999 | Bowers | 73/24.06 |

OTHER PUBLICATIONS

Wallace, Miniature Quartz Crystal Microbalance for Contamination Measurement. Journal of Space and Rockets, vol. 17, No.2, pp153–156, 1980.*
Bowers et al, Surface Acoustic Wave Piezoelectric Crystal Aerosol Microbalance. Rev. Sci. Instru., vol 60 pp 1297–1302, 1989.*

* cited by examiner

Primary Examiner—Christine Oda
Assistant Examiner—Brij B. Shrivastav
(74) Attorney, Agent, or Firm—Kinney & Lange, P.A.

(57) ABSTRACT

The concentration of an analyte in a fluid is measured by a quartz crystal microbalance sensor device in the fluid containing a concentration of the analyte. The sensor device exhibits a resonant frequency representative of the concentration of the analyte in the fluid. A quartz crystal microbalance reference device has a resonant frequency lower, by a predetermined amount, than the initial resonant frequency of the sensor device before the sensor device is exposed to the analyte. A signal is derived based on the difference of the resonant frequencies of the sensor and the reference device, and a first counter counts a predetermined number of cycles of the difference signal frequency to derive a sample time period. A second counter counts cycles of a clock signal frequency during the sample time period to derive a count representative of the difference signal frequency.

20 Claims, 1 Drawing Sheet

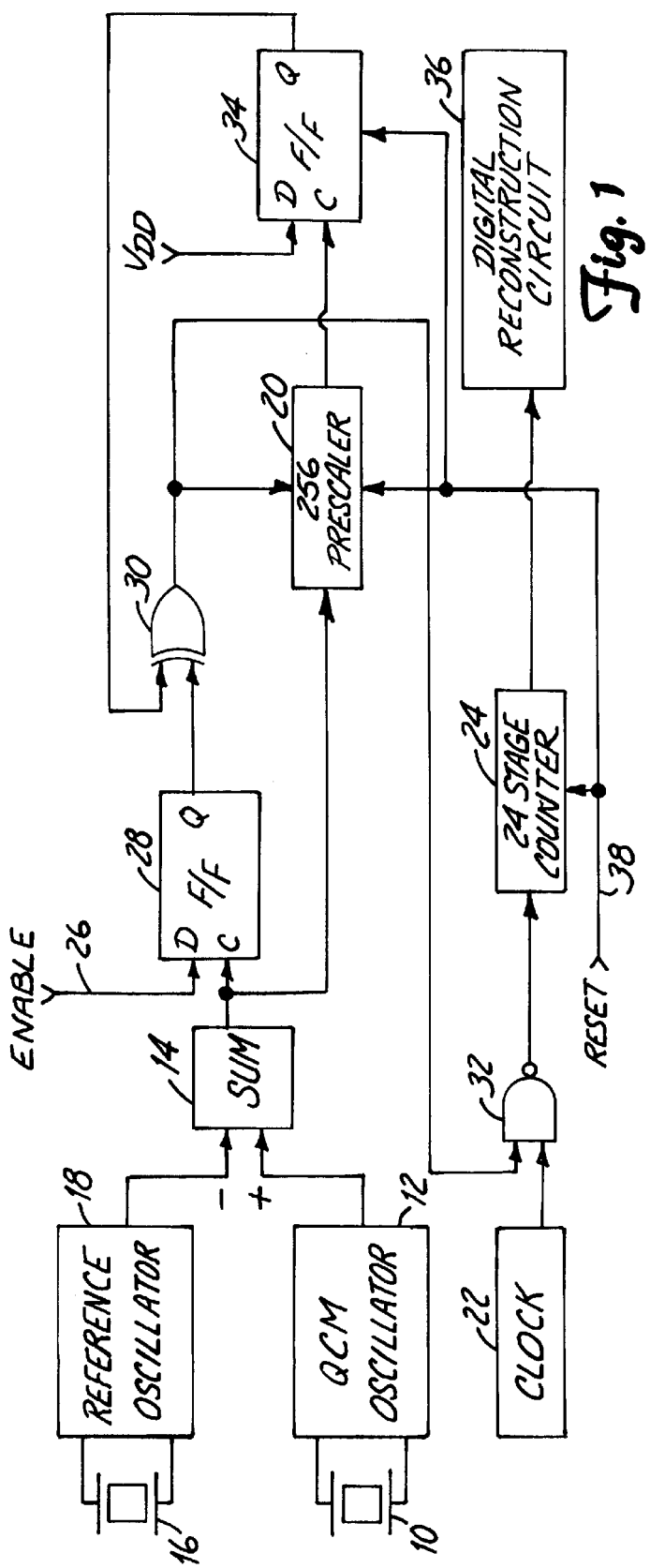
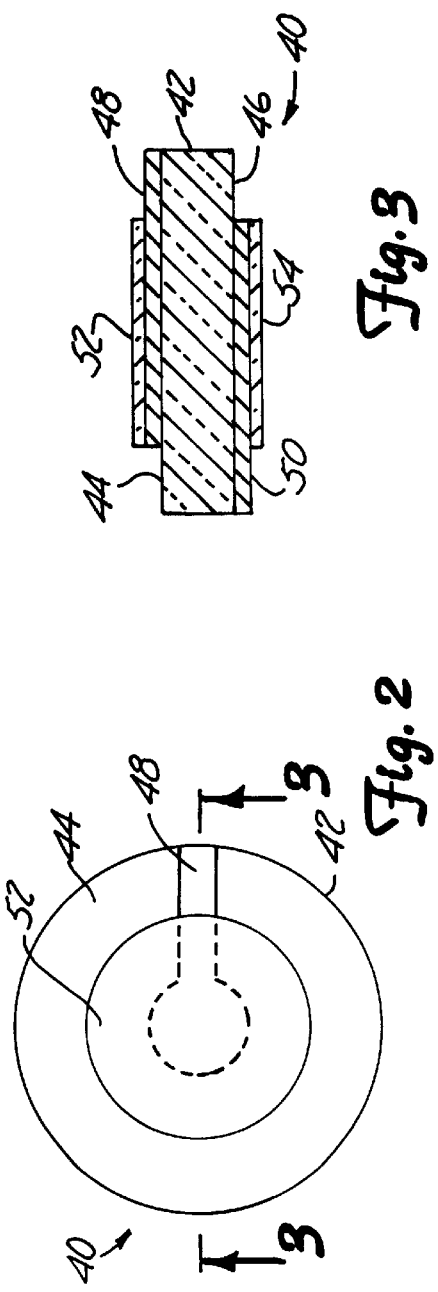

HIGH FREQUENCY MEASURING CIRCUIT WITH INHERENT NOISE REDUCTION FOR RESONATING CHEMICAL SENSORS

CROSS-REFERENCE TO RELATED APPLICATION(S)

This application is related to application Ser. No. 08/968,081 filed Nov. 12, 1997, for "High Frequency Measuring Circuit" by John P. Dilger and Nile K. Dielschneider, and assigned to the same assignee as the present application, which application is incorporated herein by reference.

BACKGROUND OF THE INVENTION

Bulk acoustic wave (BAW) chemical sensors, including quartz crystal microbalance (QCM) devices, are used to measure the concentration of constituents or analyte in fluids (gases and liquids). These acoustic wave devices are typically constructed of piezoelectric crystals coated on at least one side with a material that has an affinity for the analyte whose concentration is being measured. The device is placed in the fluid stream containing the analyte being measured, and analyte is adsorbed or absorbed onto the coated surface. The amount of analyte adsorbed or absorbed by the acoustic wave device increases the mass of the device and alters the viscoelastic properties at the surface of the device, thereby damping the acoustic wave properties of the device. As a result, the frequency at which the acoustic wave device will resonate is altered (usually lowered).

When the acoustic wave device is incorporated into an electrical oscillator circuit, the change in resonant frequency of the device changes the operating frequency of the oscillator. The concentration of the analyte can be determined by measuring the change in operating frequency of the oscillator circuit over time.

QCM devices require unique analyte-specific coatings to address sensor performance in various operational conditions. Thus, these sensors are designed to operate in specific ranges of environmental conditions, such as temperature (e.g., $-10°$ C. to $50°$ C.) and humidity (e.g., 0% to 90% relative humidity) and are capable of detecting small concentrations, and small changes of concentrations, of the targeted analyte. However, small changes in analyte concentrations can produce small changes in the resonant frequency of the crystal. In typical environments, concentrations of analyte being measured might, for example, alter the resonant frequency as little as 0.002% of the nominal resonant frequency. Thus, for a crystal having a nominal resonant frequency of 10.000 MHz, a small concentration of analyte being measured might alter the resonant frequency by about 200 Hz. Moreover, QCM devices are capable of detecting small changes in the analyte concentration through small changes in the resonant frequency. Therefore, the detection circuit must be capable to detect the resonant frequency of the crystal quite accurately, often to a resolution within about 5 Hz or less.

However, the viscoelastic properties of the device can be affected by thermodynamic conditions to which the device is subjected. More particularly, temperature and humidity "age" the characteristics of the crystal, causing permanent alteration of the viscoelastic properties of the crystal. This alteration of viscoelastic properties affects the dynamic characteristics of the device, and hence the velocity of resonance in the crystal forming the device. Alteration of the resonance properties of the crystal often creates inharmonic responses, which generates noise in the operating frequency of the oscillator circuit. Therefore, it is important to eliminate the effects of noise in the detection circuit.

The aforementioned Dilger et al. application describes apparatus for measuring changes in the resonant frequency of the sensor to a resolution of about 0.1 Hz. More particularly, Dilger et al. describe a QCM sensor exposed to an analyte to generate a resonant frequency representative of the instantaneous analyte concentration in the fluid. A first counter samples the resonant frequency over a test period to supply a coarse count. The coarse count represents a frequency that is lower that the resonant frequency of the sensor by an amount based on the resolution of the coarse count. The coarse count is converted to a signal frequency which is digitally mixed with the resonant frequency from the sensor to produce a pulse width modulated signal. The low frequency component of the pulse width modulated signal is representative of the difference between the constructed coarse frequency and the resonant frequency of the sensor. The pulse width modulated signal is filtered to remove the high frequency component, and the resulting low frequency component establishes a sample period during which a high frequency clock operates a second counter to derive a count representative of the difference frequency. The result is combined with the coarse count from the first to derive an absolute digital representation of the resonant frequency of the sensor, which is representative of the concentration of analyte. Changes in concentration can be identified from changes in the digital representation of the resonant frequency of the sensor.

The invention described in the aforementioned Dilger et al. application is effective in accurately measuring analyte concentration in fluids. More particularly, small changes in analyte concentration cause small changes in the resonant frequency of the sensor which are detected by the relatively large change in difference frequency count based on the filtered pulse width modulated signal. While the Dilger et al. apparatus is highly effective, the resolution often exceeds the requirements and capabilities of the equipment and conditions being monitored. Moreover, the apparatus requires significant computational resources and power. Accordingly, there is a need for a simpler system that does not require such extensive computational resources and power.

BRIEF SUMMARY OF THE INVENTION

This invention utilizes time domain signal processing to increase the signal-to-noise ratio of resonating QCMs.

In one form of the invention, the analyte concentration in a fluid is measured by placing a quartz crystal microbalance sensor device in the fluid. A quartz crystal microbalance reference device provides a resonant frequency representative of the resonant frequency of the sensor device when the sensor device is not exposed to the analyte. The resonant frequencies of the sensor device and the reference device are summed to provide a difference signal frequency representative of the difference between the resonant frequencies of the sensor device and the reference device. A predetermined number of cycles of the difference signal frequency is counted to identify a sample time period. A clock provides a clock signal frequency whose cycles are counted for the duration of the sample time period to derive a count representative of the difference signal frequency. Small changes in the difference frequency due to small changes in the analyte concentration sensed by the sensor device are sensed with respect to the difference frequency.

In another form of the invention, a circuit is provided for measuring the analyte concentration in the fluid. A quartz crystal microbalance sensor device is connected to a first resonator circuit and is exposed to the fluid containing a concentration of the analyte. The sensor device provides a resonant frequency representative of the analyte concentration in the fluid. A quartz crystal microbalance reference device is connected to a second resonator circuit to provide a resonant frequency different from the resonant frequency of the sensor device before the sensor device is exposed to the analyte. A digital differencing circuit is connected to the first and second resonant circuits to provide a signal representative of a sample time period that represents the difference between the resonant frequency of the sensor device and the resonant frequency of the reference device. A counter is connected to the digital differencing circuit and is responsive to the clock signal to advance the count during the sample period. The resulting count in the counter is representative of the difference between the resonant frequencies of the sensor device and the reference device.

In a preferred embodiment of the circuit, the digital differencing circuit includes a summing circuit connected to the first and second resonator circuits to provide a signal having a frequency representative of the difference between the resonant frequency of the sensor device and the resonant frequency of the reference device. A second counter is connected to the summing circuit for counting the cycles of the difference frequency, the second counter advancing its count to a predetermined count to provide a signal to the first counter representative of the sample period.

In a preferred form of this embodiment, enable means simultaneously enables the first and second counters to begin advance of their respective counts, and the first counter is responsive to the signal from the second counter to terminate its advance in count. Logic devices enable both counters when an enable signal is provided to the circuit, and disables the first counter when the second counter counts to the predetermined count.

In another preferred embodiment, the sensor device and the reference device each includes a crystal substrate having first and second electrodes, with the second electrode of each device being of different thickness. As a result, the resonant frequency of the reference device is different from the initial resonant frequency of the sensor device by a design amount, thereby optimizing the operation of the circuit.

In another form of the invention, a process for manufacturing matched quartz crystal microbalance chemical device includes providing first and second crystal substrates each having first and second opposite surfaces defining a predetermined thickness. A first electrode and a layer of material having an affinity to the analyte are formed on the first surface of the first substrate. A second electrode and a layer of material having an affinity to the analyte are formed on the first surface of the second substrate. The first electrodes are arranged so that at least a portion of the material having an affinity to the analyte confronts the respective first surface. A third electrode is formed on the second surface of the first substrate and a fourth electrode is formed on the second surface of the second substrate. The third and fourth electrodes have different thicknesses so that the first and second crystal substrates resonate at initial resonant frequencies that differ by a design amount.

BRIEF DESCRIPTION OF THE DRAWINGS

FIG. 1 is a block diagram of the measuring system employing noise reduction in accordance with the presently preferred embodiment of the present invention.

FIG. 2 is a plan view of a sensor for use in the system of FIG. 1.

FIG. 3 is a section view of the sensor taken at line 3—3 in FIG. 2.

DETAILED DESCRIPTION

FIG. 1 is a block circuit diagram of a circuit for measuring analyte concentrations in fluids in accordance with the presently-preferred embodiment of the present invention. A first bulk acoustic wave (BAW) chemical sensor, such as a quartz crystal microbalance (QCM) device 10, is exposed to the fluid carrying the analyte to be measured and provides input to QCM parallel resonant circuit 12 to form an oscillating circuit designed to oscillate at the resonant frequency of device 10. In a preferred form of the invention, circuit 12 includes a pair of NAND gates and an AND gate that operate to oscillate at the resonant frequency of QCM sensor 10. In a preferred form of the invention, circuit 12 is constructed as described in the aforementioned Dilger et al. application. Circuit 12 provides an output signal, at the resonant frequency of device 10 to a first, additive, input of summing circuit 14. A second QCM sensing device 16 is connected to parallel resonant circuit 18 to provide a reference signal frequency to a second, or subtractive, side of summing circuit 14. Sensor 16 is similar to sensor 10, except that it is constructed to exhibit a resonant frequency slightly different from (preferably below) the resonant frequency of sensor 10, and sensor 16 is not exposed to the fluid containing the analyte being measured. Circuit 18 is preferably constructed identically to circuit 12. Thus, sensor 16 and circuit 18 provide a reference signal frequency slightly below the nominal frequency of sensor 10 and circuit 12. In the example to be given, the reference frequency of sensor 16 and circuit 18 is about 200 KHz below the nominal 12 MHz frequency of sensor 10 and circuit 12. Hence, circuits 12 and 18 provide signals representing an initial difference frequency $\Delta f$ of about 200 KHz. Because the reference frequency of circuit 18 is initially about 200 KHz below the sensor frequency of circuit 12, the signal frequency output of summing circuit 14 is $\Delta f$. The 200 KHz difference frequency is chosen because that difference frequency is greater than any expected change in resonant frequency of sensor 10 due to expected analyte concentrations, yet the difference frequency is small enough to permit small changes in resonant frequency of sensor 10 to be adequately measured against the difference frequency.

As explained above, analyte adsorbed or absorbed by the coated surface of sensor 10 lowers the resonant frequency of sensor 10 by an amount representative of the concentration of the analyte being measured in the fluid under test. Consequently, the frequency of the signal supplied by circuit 12 to summing circuit 14 will be different (lower) from its nominal frequency by an amount representative of the analyte concentration in the fluid. As a result the difference frequency $\Delta f$ changes (decreases), also by an amount representative of the analyte concentration.

Summing device 14 provides an output representative of the instantaneous difference $\Delta f$ of the signal frequencies from circuits 12 and 18. The output of summing circuit 14 is provided to 256 prescaler 20 which is an 8-bit counter arranged to count the cycles of the difference frequency from summing circuit 14 and provide an output signal when 256 transitions have been detected. More particularly, prescaler 20 senses the positive slope or edge of each cycle of the difference frequency signal from summing circuit 14 to count the 256 cycles of difference signal frequency.

Clock circuit 22 is a free-running clock circuit that supplies a signal at a fixed frequency, significantly higher than the frequency of either crystal 10 or 16, to 24-stage counter 24. Counter 24 is a 24-bit counter that counts up to $2^{24}$ cycles of the clock signal from clock 22. More particularly, counter 24 is responsive to the positive slope or edge of each cycle of clock signal to advance the count in counter 24.

Prescaler 20 and counter 24 are simultaneously enabled by a signal from enable 26, through D-type flip-flop 28 to synchronize prescaler 20 and counter 24 with signals from summing circuit 14. More particularly, the difference frequency signal Δf is input to the clock input of flip-flop 28 so that when the enable signal at 26 is set high, flip-flop 28 provides a high signal output upon the next high input from summing circuit 14 (i.e., when Δf goes high). The high output from flip-flop 28 is provided to one input of Exclusive-OR gate 30. Assuming the other input of gate 30 is low, gate 30 provides an enable signal to the enable input of prescaler 20, and to AND gate 32. Prescaler 20 thus responds to the next positive signal cycle of Δf from summing circuit 14 to begin counting difference frequency signal cycles. Simultaneously, gate 32 responds to the enabling signal from gate 30 to pass inverted clock signals from clock 22 to counter 24 to thereby advance the count in counter 24.

When prescaler 20 reaches its full count (e.g., having counted 256 cycles of the Δf signal from summing circuit 14) prescaler 20 provides an output which serves to disable counter 24. More particularly, the high output from prescaler 20 signifying the full count of the prescaler is applied to the clock input of D-type flip-flop 34, whose D input is connected to a positive supply $V_{DD}$. Flip-flop 34 thus provides a high output to the second input of Exclusive-OR gate 30, forcing the output of gate 30 low, removing the enable from prescaler 20 and forcing the input to gate 32 low. With the input of gate 32 low, gate 32 ceases passing clock signals from clock 22, thereby halting the advance of count in counter 24. Thus, counter 24 counts clock signal cycles from clock 22 for a period of time that is representative of 256 cycles of difference signal frequency from summation device 14. The count in counter 24, which is representative of an averaged difference signal frequency from summing circuit 14, is supplied to digital reconstruction circuit 36 to construct a representation of the average of the difference frequency over the period of the count of prescaler 20. By iteratively sensing successive representations of the difference signal frequency, the concentration of the analyte in the fluid under test can be measured. Thus, meaningful information is provided concerning the concentration of the analyte affecting sensor 10 that altered the resonant frequency of sensor 10.

Sensors 10 and 16 are constructed so that sensor 16 has a resonant frequency different from the resonant frequency of sensor 10 by a predetermined amount (e.g., 200 KHz). The preferred technique to achieve the controlled frequency difference is explained with reference to the sensor 40 illustrated in FIGS. 2 and 3. A pair of crystal substrates 42 have opposite surfaces 44 and 46 to define a thickness of substrates 42 that in part defines the equivalent resonant frequency of the device. Gold electrodes 48 and 50 are deposited to a thickness of about 3000 Angstroms onto a 50 Angstrom chromium seedlayer on opposite surfaces 44 and 46 of substrate 42. Electrodes 48 and 50 include terminals for connection of the respective sensor to respective resonant circuits 12 and 18. A 0.1 to 8 micron layer 52 of polymer material having an affinity for the analyte to be measured is deposited onto electrode 48. Optionally, a second layer 54 of the same polymer material is deposited onto electrode 50.

The nominal resonant frequency of the device is based on the crystal substrate, thickness of electrodes 48 and 50, and thickness of layers 52 and 54. To achieve a design difference in resonant frequency between sensor 10 and reference device 16, it is preferred that electrode 50 of reference device 16 is deposited to a thicker layer than corresponding electrode 50 of sensor 10. By controlling the thickness of deposit of electrode 50, the resonant frequency of the corresponding device can be precisely controlled. The mass of electrode 50 affects the resonant frequency of the device. Therefore, for sensors exhibiting equal temperature coefficients and otherwise equal physical dimensions, those sensors with a greater thickness or mass to electrode 50 will exhibit a predetermined different resonant frequency than the similar sensors with a smaller thickness or mass to electrode 50. The greater mass or thickness to electrode 50 dampened propagation of the resonant wave through the respective crystal, thereby reducing the resonant frequency by the design amount. Consequently, precise control over the difference frequency between sensor 10 and reference device 16 can be achieved.

Conveniently, the sensor and reference devices 10 and 16 may be manufactured together from the same substrate, thereby assuring manufacturing consistency to the mating or complementing pair of devices so that the devices may be used together in the circuit. The devices are processed together through manufacturing until deposition of electrode 50, where a greater thickness is applied to the reference device electrode than to the sensor device electrode. As a less desirable approach, one or both coatings 52 and/or 54 of reference device 16 is deposited to a greater thickness than the same coatings of sensor 10, again to increase the mass of the reference device and lower its resonant frequency by a design amount. In either case, the reference device and sensor device exhibit a specific design difference frequency. In either case, the resonant frequency of the device may be monitored during manufacture by a frequency counter to determine final frequency.

Operation of the circuit illustrated in the drawing may best be explained by an example where sensor 10 and resonant circuit 12 are designed to provide an initial signal frequency of 12.000 MHz (in absence of analyte), reference crystal 16 and resonant circuit 18 are designed to provide a reference frequency of 11.800 MHz, and clock 22 provides a signal of 50 MHz. Summing circuit 14, therefore, initially provides an output signal representative of the frequency difference of the signals from circuits 12 and 18, namely 200 KHz, to prescaler 20.

Enable signal 26 is applied to flip-flop 28 to simultaneously begin advance of the counts in prescaler 20 and counter 24. More particularly, upon the next positive signal from summing circuit 14 following application of the enable signal, flip-flop 28 operates gate 30 to provide an enable signal to prescaler 30 so that prescaler 20 begins counting difference frequency signal Δf cycles from summing circuit 14. Simultaneously, gate 30 provides an enable signal to gate 32 so that gate 32 passes clock signals from clock 22 to counter 24 to begin counting cycles of the clock signal. In the example, prescaler 20 advances one count each $5 \times 10^{-6}$ seconds while counter 24 advances its count each $0.02 \times 10^{-6}$ seconds. When the count in prescaler 20 reaches 256, prescaler supplies a disable signal through flip-flop 34 to gate 30 to stop the advance of count by counter 24. More particularly, with both inputs of Exclusive-OR gate 30 now high, the output of gate 30 is forced low, removing the enable input from both prescaler 20 and gate 32. Thus, in the example, prescaler 20 operates counter 24 for a period of $1.28 \times 10^{-3}$ seconds. During this period of time ($1.28 \times 10^{-3}$ seconds) the count in counter 24 will have advanced by $64 \times 10^3$ counts due to the 50 MHz clock input. Thus, upon halt of counter 24, counter 24 will have advanced in count to $64 \times 10^3$.

The average difference frequency during the sample period ($1.28 \times 10^{-3}$ seconds) is determined from the count in counter 24. Thus, the total count of prescaler 20 (256) is multiplied by the frequency of clock 22 (50 MHz) and the product is divided by the count in counter 24 (e.g., $64 \times 10^3$), which yields an average difference frequency of 200 KHz.

After each iteration, the enable signal 26 is removed from the D-input of flip-flop 28 to force the Q-output of flip-flop 28 low and a reset signal 38 is provided to prescaler 20 and counter 24 to reset the counts therein to zero. The reset signal is also applied to flip-flop 34 to set its Q-output low, thereby resetting the circuit for the next iteration.

If at the next iteration the analyte in the fluid to which sensor 10 is exposed alters the resonant frequency of sensor 10 by 50 Hz to 11.79995 MHz, the sample period established by prescaler 20 is slightly longer, resulting in a slightly increased count by counter 24. In this case, the total count of prescaler 20 (256) is again multiplied by the frequency of clock 22 (50 MHz) and the product is divided by the count in counter 24 which is slightly greater than before, yielding a slightly smaller average difference frequency of 199.95 KHz.

The resolution of the circuit is based on the difference frequency from summing circuit 14 and the frequency of clock 22. More particularly, the resolution is equal to the difference frequency divided by the number of counts of counter 24 counting cycles from clock 22 during the period established by prescaler 20. In the example, with a nominal difference frequency of 200 KHz and a clock frequency of 50 MHz, the resolution of the circuit is 3.125 Hz. This means each count in counter 24 represents 3.125 Hz of difference frequency, and the concentration of the analyte being measured can be measured to an accuracy of ±1.5625 Hz.

It is evident that the resolution of the circuit is affected by changes in the difference frequency $\Delta f$ and the clock frequency of clock 22. The resolution will increase (smaller difference frequency per count in counter 24) with decreasing difference frequency $\Delta f$, and will decrease (greater difference frequency per count) with decreasing clock 22 signal frequency. For this reason, it is desirable to maintain the frequency of clock 22 as high as practical (recognizing that increased clock 22 frequency requires a larger counter 24). Moreover, by establishing an initial difference frequency $\Delta f$ that is optimally designed to the sensitivity of the system, and with $\Delta f$ becoming smaller with increasing concentration of analyte, resolution of the system is optimized.

While the clock frequency of clock 22 may be any convenient frequency and the size of counter 24 may be any convenient size, it is important that the size of counter 24 exceed any maximum count of the clock frequency that may be expected during the sampling period established by the size of prescaler 20 and a minimum difference frequency from summing circuit 14. The 24-stage counter and the 50 MHz clock frequency are such that the count in counter 24 will not ordinarily exceed the maximum of the counter. For example, the $64 \times 10^3$ counts during a sampling period established by a 200 KHz difference signal will only advance to about 16 stages of the 24 stage counter.

The apparatus of the present invention effectively reduces inherent noise due to changing thermodynamic conditions at the sensor by averaging out the difference frequency signal over a time span of 256 difference frequency cycles. Hence, small instantaneous changes occurring during the sampling period are averaged over the period, resulting in minimization of the effects of noise. The circuit time averages the difference frequency signal thereby reducing noise from the sensor. Due to the simplicity of the circuit, the circuit can be easily implemented in a semi-custom IC chip. Efficient data acquisition and signal processing is achieved by the summing circuit processing the relatively high frequency difference signal, rather than a lower frequency change in difference signal. By exposing the reference QCM 16 to the same or similar environmental conditions (temperature and humidity), but not to the analyte whose concentration is being measured, the reference clock signal frequency changes with temperature and humidity variations, thereby inherently adjusting the circuit to external environmental conditions.

Although the present invention has been described with reference to preferred embodiments, workers skilled in the art will recognize that changes may be made in form and detail without departing from the spirit and scope of the invention.

What is claimed is:

1. A process for measuring concentration of analyte in a fluid comprising:

placing a quartz crystal microbalance sensor device in the fluid containing the analyte, the sensor device having a resonant frequency based on the concentration of the analyte in the fluid and having an initial resonant frequency before the sensor device is exposed to the analyte;

providing a quartz crystal microbalance reference device, the reference device having a resonant frequency in predetermined relation to the initial resonant frequency of the sensor device;

summing the resonant frequencies of the sensor device and the reference device to provide a difference signal frequency representative of the difference between the resonant frequencies of the sensor device and the reference device;

counting a predetermined number of cycles of the difference signal frequency to identify a sample time period; and counting cycles of a clock signal frequency during the sample time period to derive a count representative of the difference signal frequency.

2. The process ofclaim 1, further including simultaneously commencing counting the cycles of difference signal and cycles of clock signal, wherein the counting of cycles of clock signal occurs for the sample time period established while the predetermined number of cycles of the difference signal is being counted.

3. A circuit for measuring concentration of a analyte in a fluid comprising:

a quartz crystal microbalance sensor device connected to a first resonator circuit, the sensor device being exposed to the fluid containing a concentration of the analyte to provide a resonant frequency representative of the concentration of the analyte in the fluid;

a quartz crystal microbalance reference device connected to a second resonator circuit to provide a resonant frequency in predetermined relationship to an initial resonant frequency of the sensor device before the sensor device is exposed to the analyte;

a timer connected to the first and second resonant circuits to provide a sample period representative of the difference between the resonant frequency of the sensor device and the resonant frequency of the reference device;

a source of clock signals; and a first counter connected to the source of clock signals and to the timer for advancing a count based on the clock signals during the sample period, the count at the end of the sample period representing the difference between the resonant frequency of the sensor device and the resonant frequency of the reference device.

4. The circuit of claim 3, wherein the timer includes a summing circuit connected to the first and second resonant circuits to provide a difference signal having a frequency representative of the difference between the resonant frequency of the sensor device and the resonant frequency of the reference device, and a second counter connected to the summing circuit for advancing a count at a rate based on the difference signal frequency, the second counter advancing its count to a predetermined count to provide a signal representative of the sample period.

5. The circuit of claim 4, further including enable means for simultaneously enabling the first and second counters to advance their respective counts, the first counter being responsive to the signal from the second counter to terminate the advance in count in the first counter.

6. The circuit of claim 5, wherein the quartz crystal microbalance sensor device comprises:
   a first crystal substrate having first and second opposite surfaces defining a predetermined thickness,
   a first electrode on the first surface,
   a second electrode on the second surface, and
   a first layer of material having an affinity to the predetermined analyte on at least a portion of the first electrode and the first surface,
   the first and second electrodes and the first layer having respective thicknesses so that the first crystal substrate resonates at a first predetermined initial frequency, the first crystal substrate changing its resonant frequency upon exposure of the exposed portion of the first layer of the crystal to the predetermined analyte, and the quartz crystal microbalance reference device comprises:
   a second crystal substrate having third and fourth opposite surfaces defining a predetermined thickness substantially equal to the predetermined thickness of the first crystal substrate,
   a third electrode on the third surface,
   a fourth electrode on the fourth surface, and
   a second layer of material having an affinity to the predetermined analyte on at least a portion of the third electrode and the third surface,
   the third and fourth electrodes and the second layer having respective thicknesses so that the second crystal substrate resonates at a second predetermined frequency, the thickness of at least one of the second layer and the fourth electrode being different from the respective first layer or second electrode so that the second predetermined frequency is different from the first predetermined initial frequency by a design amount.

7. The circuit of claim 6, wherein the thickness of the fourth electrode is greater than the thickness of the second electrode so that the second predetermined frequency is lower than the first predetermined frequency by the design amount.

8. The circuit of claim 5, wherein the enable means includes a first bistable device having an output, an enable input and a clock input, the enable input receiving an enable signal for initiating the sample period and the clock input being connected to the summing means to produce an output signal at the first bistable device output upon receipt of a cycle of difference signal frequency first following receipt of the enable signal, the second counter having an enable input responsive to the output signal from the first bistable device to initiate advance of count, a first gate having an output, an enable input and a clock input, the clock input being connected to the source of clock signals and the enable input being responsive to the output signal from the first bistable device to initiate passage of clock signals from the source of clock signals to the first gate output, and the first counter being connected to the output of the first gate and responsive to clock signals from the first gate to advance in count.

9. The circuit of claim 8, including a second bistable device having a clock input and an output, the clock input of the second bistable device being connected to the output of the second counter, the second bistable device being responsive to a predetermined count in the second counter to provide a signal at its output, and a second gate having first and second inputs and an output, the first input of the second gate being connected to the output of the first bistable device, the second input of the second gate being connected to the output of the second bistable device, and the output of the second gate being connected to the enable inputs of the second counter and the first gate, the second gate being responsive to the output signal from the first bistable device to simultaneously initiate advance of counts by the first and second counters and being responsive to the output signal from the second bistable device to simultaneously disable the second counter and the first gate.

10. The circuit of claim 8, wherein the quartz crystal microbalance sensor device comprises:
   a first crystal substrate having first and second opposite surfaces defining a predetermined thickness,
   a first electrode on the first surface,
   a second electrode on the second surface, and
   a first layer of material having an affinity to the predetermined analyte on at least a portion of the first electrode and the first surface,
   the first and second electrodes and the first layer having respective thicknesses so that the first crystal substrate resonates at a first predetermined initial frequency, the first crystal substrate changing its resonant frequency upon exposure of the exposed portion of the first layer of the crystal to the predetermined analyte, and the quartz crystal microbalance reference device comprises:
   a second crystal substrate having third and fourth opposite surfaces defining a predetermined thickness substantially equal to the predetermined thickness of the first crystal substrate,
   a third electrode on the third surface,
   a fourth electrode on the fourth surface, and
   a second layer of material having an affinity to the predetermined analyte on at least a portion of the third electrode and the third surface, the third and fourth electrodes and the second layer having respective thicknesses so that the second crystal substrate resonates at a second predetermined frequency, the thickness of at least one of the second layer and the fourth electrode being different from the respective first layer or second electrode so that the second predetermined frequency is different from the first predetermined initial frequency by a design amount.

11. The circuit of claim 10, wherein the thickness of the fourth electrode is greater than the thickness of the second electrode so that the second predetermined frequency is lower than the first predetermined frequency by the design amount.

12. The circuit of claim 3, wherein the quartz crystal microbalance sensor device comprises:
   a first crystal substrate having first and second opposite surfaces defining a predetermined thickness,
   a first electrode on the first surface,
   a second electrode on the second surface, and
   a first layer of material having an affinity to the predetermined analyte on at least a portion of the first electrode and the first surface,
   the first and second electrodes and the first layer having respective thicknesses so that the first crystal substrate resonates at a first predetermined initial frequency, the first crystal substrate changing its resonant frequency upon exposure of the exposed portion of the first layer of the crystal to the predetermined analyte, and the quartz crystal microbalance reference device comprises:
   a second crystal substrate having third and fourth opposite surfaces defining a predetermined thickness substantially equal to the predetermined thickness of the first crystal substrate,
   a third electrode on the third surface,
   a fourth electrode on the fourth surface, and
   a second layer of material having an affinity to the predetermined analyte on at least a portion of the third electrode and the third surface,
   the third and fourth electrodes and the second layer having respective thicknesses so that the second crystal substrate resonates at a second predetermined frequency, the thickness of at least one of the second layer and the fourth electrode being different from the respective first layer or second electrode so that the second predetermined frequency is different from the first predetermined initial frequency by a design amount.

13. The circuit of claim 12, wherein the thickness of the fourth electrode is greater than the thickness of the second electrode so that the second predetermined frequency is lower than the first predetermined frequency by the design amount.

14. The circuit of claim 12, wherein the thickness of the fourth electrode is greater than the thickness of the second electrode.

15. The circuit of claim 12, wherein the thickness of the second layer is greater than the thickness of the first layer.

16. A process for manufacturing complementing quartz crystal microbalance chemical devices for use together in a circuit to measure concentration of an analyte in a fluid, the process comprising:

providing first and second crystal substrates each having first and second opposite surfaces defining a predetermined thickness, the predetermined thicknesses of the first and second substrates being substantially equal;

forming a first electrode on the first surface of the first substrate and forming a second electrode on the first surface of the second substrate, the first and second electrodes being configured to expose at least a portion of the respective first surface and formed to have substantially equal thicknesses;

forming a first layer of selected material having an affinity to the analyte on at least a portion of the first electrode and the first surface of the first substrate and forming a second layer of the selected material on at least a portion of the second electrode and the first surface of the second substrate; and forming a third electrode on the second surface of the first substrate and forming a fourth electrode on the second surface of the second substrate, the first and second layers of selected material and the third and fourth electrodes being so disposed and arranged that the respective first and second crystal substrates resonate at different initial resonant frequencies, the initial resonant frequencies differing from each other by a design amount.

17. The process of claim 16, wherein the first, second, third and fourth electrodes are formed by depositing electrode material onto the respective surface of the respective substrate, the fourth electrode being deposited to a thickness greater than the thickness of the third electrode so that the second crystal substrate has an initial resonant frequency that is lower than the initial resonant frequency of the first crystal substrate by the design amount.

18. The process of claim 16, wherein forming the first layer of selected material includes forming a third layer of the selected material on at least a portion of the third electrode and the second surface of the first substrate, and forming the second layer of selected material includes forming a fourth layer of the selected material on at least a portion of the second electrode and the first surface of the second substrate, the fourth layer of selected material having a thickness greater than the thickness of the third layer of selected material so that the second crystal substrate has an initial resonant frequency that is lower than the initial resonant frequency of the first crystal substrate by the design amount.

19. An average frequency sampling circuit for sampling an average frequency of an input signal, comprising a first bistable device having an output, an enable input and a clock input, the first bistable device being responsive to an enable signal at the enable input and the input signal at the clock input to produce an output signal at the first bistable device output upon receipt of a cycle of input signal first following the enable signal;

a first counter for counting a predetermined number of cycles of the input signal, the first counter having an enable input responsive to the output signal from the first bistable device to initiate advance of count;

a clock providing a clock signal at a predetermined frequency higher than the expected frequency of the input signal;

a first gate having an output, an enable input and a clock input, the clock input being connected to the clock to receive clock signals and the enable input being responsive to the output signal from the first bistable device to initiate passage of clock signals from the clock to the first gate output; and a second counter connected to the first gate output for counting cycles of the clock signal, the second counter being responsive to the first counter advancing to a predetermined count to halt counting cycles of the clock signal.

20. The average frequency sampling circuit of claim 19, including a second bistable device having a clock input and an output, the clock input of the second bistable device being connected to the output of the first counter, the second bistable device being responsive to a predetermined count in the first counter to provide a signal at its output, and a second gate having first and second inputs and an output, the first input of the second gate being connected to the output of the first bistable device, the second input of the second gate being connected to the output of the second bistable device, and the output of the second gate being connected to the enable inputs of the first counter and the first gate, the second gate being responsive to the output signal from the first bistable device to simultaneously initiate advance of counts by the first and second counters and being responsive to the output signal from the second bistable device to simultaneously disable the first counter and the first gate.

* * * * *